US006971388B1

(12) United States Patent
Michaels

(10) Patent No.: US 6,971,388 B1
(45) Date of Patent: Dec. 6, 2005

(54) INTERNAL NASAL DILATOR FILTER

(75) Inventor: Robert C. Michaels, Santa Barbara, CA (US)

(73) Assignee: Santa Barbara Medco, Inc., Santa Barbara, CA (US)

( * ) Notice: Subject to any disclaimer, the term of this patent is extended or adjusted under 35 U.S.C. 154(b) by 0 days.

(21) Appl. No.: 11/086,710

(22) Filed: Mar. 21, 2005

(51) Int. Cl.$^7$ ............................................ A61M 15/00
(52) U.S. Cl. ............ 128/206.11; 128/858; 128/204.12; 606/199
(58) Field of Search .......................... 128/207.18, 858, 128/206.11, 204.12, 204.13; 606/199, 204.45

(56) References Cited

U.S. PATENT DOCUMENTS

| | | | | |
|---|---|---|---|---|
| 113,675 | A | * | 4/1871 | Dixon .............................. 57/18 |
| 513,458 | A | * | 1/1894 | Dayton ........................ 606/199 |
| 851,048 | A | * | 4/1907 | Woodward .................. 606/199 |
| 1,014,076 | A | * | 1/1912 | McConnell ................. 606/199 |
| 1,014,758 | A | * | 1/1912 | Knowlson .................... 606/199 |
| 1,077,574 | A | * | 11/1913 | Woodward .................. 606/199 |
| 1,255,578 | A | * | 2/1918 | Boxley ........................ 606/199 |
| 1,481,581 | A | * | 1/1924 | Woodward .................. 606/199 |
| 1,597,331 | A | * | 8/1926 | Thurston et al. ............. 606/199 |
| 1,672,591 | A | * | 6/1928 | Wells .......................... 606/199 |
| 1,709,740 | A | * | 4/1929 | Rogers ........................ 606/199 |
| 2,264,153 | A | * | 11/1941 | Rowe ..................... 128/204.12 |
| 2,426,161 | A | * | 8/1947 | Biederman ............. 128/204.12 |
| 2,515,756 | A | * | 7/1950 | Bove ........................... 606/199 |
| 2,672,138 | A | * | 3/1954 | Carlock ................. 128/207.18 |
| 3,460,533 | A | * | 8/1969 | Pla ......................... 128/207.18 |
| 3,710,799 | A | * | 1/1973 | Caballero .................... 606/199 |
| 4,201,217 | A | * | 5/1980 | Slater ........................... 606/199 |
| 4,414,977 | A | * | 11/1983 | Rezakhany .................. 606/199 |
| 4,759,365 | A | * | 7/1988 | Askinazy ..................... 606/199 |
| 5,350,396 | A | * | 9/1994 | Eliachar ...................... 606/199 |
| 5,425,359 | A | * | 6/1995 | Liou ....................... 128/206.11 |
| 5,479,944 | A | * | 1/1996 | Petruson ..................... 128/858 |
| 5,816,241 | A | * | 10/1998 | Cook ..................... 128/200.24 |
| 5,895,409 | A | * | 4/1999 | Mehdizadeh ................ 606/199 |
| 5,922,006 | A | * | 7/1999 | Sugerman .............. 606/204.45 |
| 6,106,541 | A | * | 8/2000 | Hurbis ......................... 606/199 |
| 6,238,411 | B1 | * | 5/2001 | Thorner ....................... 606/199 |
| 6,270,512 | B1 | * | 8/2001 | Rittmann ..................... 606/199 |
| 6,328,754 | B1 | * | 12/2001 | Marten et al. .............. 606/199 |
| 6,562,057 | B2 | * | 5/2003 | Santin ......................... 606/199 |
| 2003/0144684 | A1 | * | 7/2003 | Ogle ........................... 606/199 |
| 2004/0059368 | A1 | * | 3/2004 | Maryanka ................... 606/191 |
| 2004/0147954 | A1 | * | 7/2004 | Wood .......................... 606/199 |

FOREIGN PATENT DOCUMENTS

| | | | |
|---|---|---|---|
| CH | 689199 | * | 12/1998 |
| DE | 19736717 | * | 4/1998 |

* cited by examiner

*Primary Examiner*—Henry Bennett
*Assistant Examiner*—Dinnatia Doster-Greene
(74) *Attorney, Agent, or Firm*—Felix L. Fischer

(57) ABSTRACT

A device combining internal nasal filtration and internal nasal dilation operating synchronously provides air filtration by retaining particulate in a single piece foam nasal filter during inhalation through the nose. Internal nasal dilation is provided by the effect of a resilient member adhesively affixed to the nasal foam filter and which when bent from a planar surface applies outward biasing forces to each nostril so that breathing is facilitated. The soft, gentle foam of the nasal filter distributes the biasing forces over a large area and protects the inside of the nose from irritation. An improved internal nasal dilator filter functions to provide increased air flow through dilation while removing various sizes of particulate through filtration.

16 Claims, 5 Drawing Sheets

INTERNAL NASAL DILATOR FILTER

BACKGROUND OF THE INVENTION

1. Field of the Invention

This invention relates generally to the field of nasal dilators and air filtration and, more particularly, to an interal nasal dilator incorporating filtration having two semi-spherically topped substantially cylindrical reticulated foam depth filters with an integral interconnecting resilient member and arculate band set for insertion into the user's nostrils for nasal dilation and air filtration.

2. Description of the Related Art

Millions of people suffer from nasal obstructions or physiological conditions that make nasal breathing difficult, uncomfortable, or impossible. Examples of such conditions include narrowing of the nasal valve, allergic reactions, enlarged adenoid tissue and swollen nasal mucosa. The nasal valve, named by P.S. Mink in 1903 is the narrowest area in the nasal cavity, the adjacent area being larger both upstream and downstream. The nasal valve is located at the junction of the upper lateral and lower lateral cartilages about one third of the way from the tip of the nose.

The mucus membranes in the nasal valve area are extremely vascular. Any inflammation in this area causes swelling of the vascular tissue, narrowing down the nasal valve space and causing difficulty breathing. Decongestants can often help to reduce the swelling and make it easier to breathe. However, they can have a deleterious effect after several days of use and may cause an increase in swelling.

The airflow resistance provided by the nasal airways during breathing is essential for good pulmonary function. The nose is responsible for most of this resistance and consequently within the nasal air passageways, the nasal valve functions as a sort of flow limiting device. However, if the nasal valve area is reduced due to mucusal swelling or because the outer wall tissue of the nasal passage draws in during inhalation, breathing through the nose becomes difficult creating a tendency to mouth breathe.

Breathing through the mouth bypasses the natural air handling system of the body thereby negating all the built-in physiological benefits. Some reasons nasal breathing is superior include: (1) air is held in the lungs longer thus facilitating the interchange of oxygen and carbon dioxide, (2) air passing through the nasal mucosa carries the stimuli to the reflex nerves that control breathing, (3) the nostrils and cilia filter the air, (4) the sense of smell is enhanced, (5) the air is warmed, moisturized or dehumidified, (6) the tendency to snore, a precursor of sleep apnea, is reduced and (7) common cold germs and bacteria are more easily intercepted and discarded.

The advantage of breathing through the nose clearly offers significant physiological benefits. This is especially so for athletes and others who participate in strenuous physical activities such as sports. They process a far greater volume of air than more sedentary people and consequently are sensitive to restrictions in the air pathways such as the nasal valve. Clearly, any approach that mitigates a reduced nasal passageway and filters the air at the same time offers significant health benefits to the millions of people who suffer from nasal obstructions or physiological conditions that make nasal breathing difficult, uncomfortable, or impossible.

One such approach is a surgical technique using alar batten grafts as described by Becker et al, Journal of Long-Term Effects of Medical implants, 13(3)259-269 (2003). Another surgical technique is a revision rhinoplasty, internal valve stenosis as described by Becker et al. However, surgical intervention is expensive, time consuming and may not entirely ameliorate the problem.

For those seeking a non-surgical or non-pharmaceutical option, there is generally known prior art that teaches the use of nasal dilators. As defined by the Food and Drug administration, "a nasal dilator is a device intended to provide temporary relief from transient causes of breathing difficulties resulting from structural abnormalities and/or transient causes of nasal congestion associated with reduced nasal airflow." A nasal dilator, therefore, decreases airway resistance and increases nasal airflow.

There are two kinds of nasal dilators, external and internal. The external dilator, which is not a feature of the present invention, is constructed from one or more layers of material upon which a truss member is attached, with a skin adhesive applied to adhere to the outside of the nose. The external nasal dilator acts with a pulling action against the truss member to pull on the external nose tissue to open the nasal passageways. The adhesive must have enough strength to hold the dilator to the nose but not too much so that it is difficult or painful to remove. The internal nasal dilator has historically been made of metal or plastic and is placed inside the nostrils. It opens the nasal passages by pushing the nostrils open by pressing on the interior nasal side walls.

As a second alternative to a surgical approach to treat nasal obstruction, many others have proposed the use of internal nasal dilators. Unfortunately, most have overlooked the advantages of coincident filtration.

Examples of US internal nasal dilator patents include:

| Number | Year Issued | Inventor | Title |
| --- | --- | --- | --- |
| 6,328,754 | 2001 | Marten et al | Nasal dilator |
| 6,270,512 | 2001 | Jean Rittmann | Internal nasal dilator |
| 6,238,411 | 2001 | Robert Thorner | Internal nasal dilator |
| 6,106,541 | 2000 | Charles Hurbis | Surgically implanted dilator |
| 5,922,006 | 1999 | Joe Sugarman | Nasal appliance |
| 5,895,409 | 1999 | Mehdizadeh | Nasal dilator |
| 5,816,241 | 1998 | Cook | Coiled nasal dilator |
| 5,479,944 | 1996 | Bjorn Petruson | Nasal devices |
| 5,350,396 | 1994 | Isaac Eliachar | Nasal splint |
| 4,759,365 | 1988 | Leo Askinazy | Spring coil wire device |
| 4,414,977 | 1983 | Rezakhany | Nasal dilator |
| 4,201,217 | 1980 | Robert Slater | Nostril expander |
| 3,710,799 | 1973 | Carlos Caballero | Nose dilator |
| 3,460,533 | 1965 | C. Riu Pla | Nasal expander-inhaler |
| 2,515,756 | 1950 | C. Bove | Nasal appliance |
| 1,709,740 | 1929 | J. R. Rogers | Nasal distender |
| 1,672,591 | 1928 | W. A. Wells | Nostril dilation |
| 1,597,331 | 1926 | H. Thurston et al | Nostril expander |
| 1,481,581 | 1924 | H. R. Woodward | Nostril expander |
| 1,255,578 | 1918 | C. Boxley | Nasal appliance |
| 1,135,675 | 1915 | G. E. Dixon | Nostril dilating device |
| 1,077,574 | 1913 | H. R. Woodward | Nostril expander |
| 1,014,758 | 1912 | A. C. Knowlson | Nostril expanding device |
| 1,014,076 | 1912 | F. M. McConnell | Nasal expander |
| 851,048 | 1907 | H. R. Woodward | Nostril expander |
| 513,458 | 1894 | W. A. Dayton | Nasal expander |

Examples of US internal nasal dilator patent application publications include:

| Number | Year Pub. | Inventor | Title |
| --- | --- | --- | --- |
| 2004/0059368 | 2004 | Paz Maryanka | Nasal Cavity Dilator |
| 2004/0147954 | 2004 | Charles Wood | Internal nasal dilator |
| 2003/0144684 | 2003 | Ronald Ogle | Adjustable nasal dilator filter |

Examples of foreign internal nasal dilator patents include:

| Number | Year Issued | Inventor | Title | Country |
|---|---|---|---|---|
| DE19736717 | 1998 | M. F. B. Velasquez | Nostril expander | Germany |
| CH689199 | 1998 | Berthod Remy | Nasal passage expander | Switzerland |

A review of the prior art teaches that solutions were being sought for nasal breathing impediments for two centuries. Generally the devices proposed in the patents are suitable for their intended purposes but suffer from the significant disadvantage of no coincident filtration. For example, both U.S. Pat. No. 6,270,512 issued to Rittman and U.S. Pat. No. 6,238,411 issued to Thorner do not incorporate any filtration, as does the present invention. The depth filter of the present invention incorporates reticulated foam that captures and holds contaminates by providing a tortuous path for the air flow to follow as it passes through the filter media. A foam depth filter has the greatest particle retention efficiency and airflow while still maintaining the lowest pressure drop of all the common filter materials. Also, both Rittman and Thorner teach the use of a hard spring like material that fits within the nostril—0.020" gauge steel wire (Rittman) and phos-bronze spring material (Thorner). Unlike the present invention that utilizes soft gentle foam to hold the dilator in place, the use of metal spring material can be uncomfortable to insert in the nostrils and difficult to adjust for various nose shapes and sizes.

Two internal nasal dilator patent application publications U.S. 2003/0144684, Ogle and U.S. 2004/0147954, Wood, teach air filtration in addition to internal nasal dilation. Ogle teaches of two 0.050 inch diameter nylon loops joined by a retaining tube. Upon careful insertion in the nostrils the nylon loops apply an outward force to the inside of the nasal tissue walls causing dilation. Ogle also teaches that the loops will cause a static electrical charge as air moves over the nylon loops and that this charge will capture particulate. Unlike the present invention, which utilizes a highly efficient depth filter, it is unlikely that the 0.050" thick nylon loops situated in the mucosa of the inside of the nose will generate a meaningful static charge of sufficient amount to facilitate particulate capture. In addition, the loop diameter is so small that the loops may cause discomfort or erode the inside of the nose.

Wood teaches of two tapered housings that are intended to be inserted in the nostrils. The tapered housings are constructed of a resilient material configured as an open framework of tubular mesh in the manner of nasal filter prior art. Wood teaches that various filtering media can be placed within the tubular framework to filter air prior to introduction into the lungs. Unlike the present invention, which incorporates a resilient member to provide the dilation force, the tapered shape must be inserted further into the nose to achieve greater dilation. Depending upon the angle of the housing taper, the device could be very uncomfortable to insert and wear. The tapered shape is extremely stiff in the axial direction, possibly causing great discomfort during insertion. Also, there are small, difficult-to-handle pieces, the housings are not conformable to the inside of the nose and it is difficult for the housings to seal in different size nostrils thereby facilitating blowby, the passage of air between the tapered housing and the inside of the nose. Wood also teaches that the housings may be reusable possibly leading to contamination, which may be present in the nose including rhinoviruses, adenoviruses, and bacteria. Also, Wood teaches that air filtration media configured in a hollow conical shape may accomplish air filtration but presents no data to indicate that filtering or even breathing through the filter is possible. As determined by laboratory simulation, discussed later, the present invention utilizes a highly efficient depth filter rated at a retention efficiency of 97% for particulate 7 microns and larger at a flow rate of approximately 1 cubic feet per minute and a filter pressure drop of less than one inch of water.

It is therefore desirable to provide for nasal dilation and at the same time utilize a unitary foam depth filter to clean the air drawn into the lungs.

It is further desirable that an internal nasal dilator filter provide a method for dilating the nose and filtering the air inhaled through the nose by providing a reticulated foam filter shaped to be soft and gentle to the interior of the nose while effectively preventing airborne contaminates such as allergens, animal dander, house dust, mites and grass pollens from entering the respiratory system.

As opposed to a filter media with a separate piece inserted in a tapered housing, it is desirable that the filter consists of a single filter material molded into a shape that can be easily and safely inserted into and removed from the interior of the nose and nostrils. A unitary design provides the maximum surface area and volume for maximum airflow and filter efficacy.

Another desirable feature of a new internal nasal dilator filter is that when fully seated within the nostrils its appearance will be aesthetically pleasing.

It is further desirable to provide an internal nasal dilator filter that will remain in place during eating, drinking, talking and heavy exertion but may be expelled in the event of an explosive sneeze.

Additionally it is desirable to provide an internal nasal dilator filter that is easily manufactured, and intended to be disposable thereby minimizing the opportunity to reinsert a unit contaminated with viruses, bacteria and allergens.

It is also desirable to provide a simple, low cost, portable, internal nasal dilator filter that can be economically used by all members of society.

It is also desirable to utilize the natural ability of foam to expand, fill and form to the nostril area thereby sealing the internal nasal dilator filter within the nostrils, eliminating filter blow-by and providing maximum filtering area. Also it is desirable that the foam can easily be compressed both axially and radially, Further, it is desirable to utilize the inherent ability of the resilient member and foam to apply gentle pressure to expand the outer nasal wall tissues from the septum structures thereby providing nasal dilation, increased air flow and subsequent filtering efficacy.

Still further, it is desirable to provide an internal nasal dilator filter of the depth filter type which will capture and hold contaminates by providing a tortuous path for the air flow to follow as it passes through the filter media.

SUMMARY OF THE INVENTION

The present invention provides a combination of internal nasal dilation and nasal filtration operating synchronously. Given this particular combination, the increase in airflow resistance due to the foam filter is offset by the increased airflow caused by the dilation thereby providing an increase in clean air to the lungs.

Air filtration is achieved by retaining particulate in a nasal foam depth filter as air is inhaled through the nose. The filter retention efficiency is 97% for particulate 7 microns and larger at a flow of approximately 1 cubic feet per minute (I CFM) and a filter pressure drop of less than one inch of water (1" $H_2O$).

Internal nasal dilation is provided by the effect of a resilient member adhesively affixed to the nasal foam depth filter and which when bent from a planar surface applies equal outward biasing forces to the inside of the nose so that breathing is facilitated. The soft, gentle foam of the depth filter distributes the biasing force and protects the inside of the nose from irritation. The present invention thus provides an improved internal nasal dilator filter which functions to provide increased air flow through dilation while improving the quality of breathing air by removing particulate during respiration.

The present invention is a combination of internal nasal dilation and internal nasal filtration functioning synergistically to overcome nasal airflow resistance and to provide a greater quantity of filtered air to the lungs by utilizing a highly efficient depth filter to clean the air. The present invention consists of two semi-cylinders of reticulated foam filter media with a spherical shape on the distal (interior nose) end and a flat surface on the proximal end joined to each other at the proximal end with a thin flexible band. The thin flexible band is integrally molded with the semi-cylinders and is made from the same material and at the same time as the semi-cylinders.

Overlaying the thin flexible band and adhesively attached to it and both semi-cylinders is a resilient member in its normal planar orientation. Internal dilation is provided by the effect of the resilient member which when bent from a planar surface applies outward biasing forces to the inside of the nose so that breathing is facilitated. The soft, gentle foam of the filter distributes the biasing forces and protects the inside of the nose from irritation.

The resilient member and adhesively attached foam is intended to be formed into a graceful "U" shape with the resilient member to the inside of the "U." The distal, spherical shaped end of each semi-cylinder is intended to be inserted in the nostril and located just inside and within the nasal vestibule. The spherical ends guide the internal nasal dilator filter into position and prevent damage to delicate nasal membranes. The proximal end is tucked in within the nasal vestibule just behind where the ala of the nostril narrows. The resilient member and thin flexible band prevent over-insertion of the semi-cylinders and serve as a handle to remove the internal nasal dilator filter from the nose.

The energy expended and applied to the resilient member to form the "U" shape is exactly opposite to the first and second biasing force, or restoring force developed by the resilient member. So that when placed in both nostrils the internal nasal dilator filter constantly exerts an outwardly restoring force (orthogonally against the nasal tissues) of a magnitude sufficient to return the resilient member to an unbent, planar state. Therefore, various embodiments of the present invention provide a desired amount of dilation force as determined by the physical characteristics of the resilient member with differing characteristics leading to differing degrees of dilation.

BRIEF DESCRIPTION OF THE DRAWINGS

These and other features and advantages of the present invention will be better understood by reference to the following detailed description when considered in connection with the accompanying drawings wherein.

DETAILED DESCRIPTION OF THE INVENTION

Figure 1:
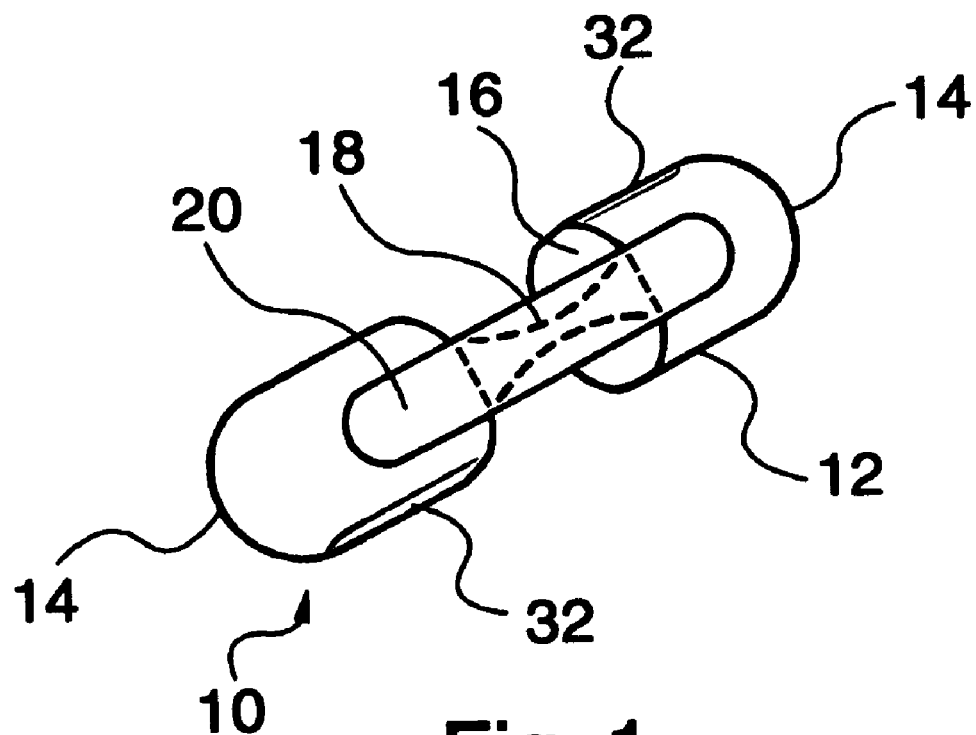
FIG. 1 is a bottom, front, left side perspective view of the internal nasal dilator filter of the present invention.

Referring to the drawings, FIG. 1 shows the assembly of the internal nasal dilator filter invention. The filter portion incorporates two semi-cylindrical shapes 12 of the same nominal diameter, which have at each distal end a spherical shape 14 to match and blend with the nominal semi-cylindrical diameter and at each other proximal end a base 16 with a flat surface whose plane is perpendicular to the cylinder axis. A thin, strong, flexible band 18 made of the same material as the semi-cylinders joins the semi-cylindrical shapes. The entire filter portion is made from the same material, reticulated foam of the polyurethane or silicone chemical family and of the polyether or polyester category. For the embodiments shown, the semi-cylindrical shapes and connecting flexible band are integrally molded, Referring again to FIG. 1, extending longitudinally along the thin, strong, flexible band 18 and further extending along a loft line of the circumferential surface of a portion of both of the semi-cylindrical shapes is a plastic, flexible resilient member 20, which for the embodiment shown is adhesively attached. FIG. 1 shows an embodiment of the present invention in the "relaxed" state. In use, the resilient member is bent into a "U" shape causing the semi-cylindrical shapes to be substantially parallel with the attachment loft lines of the circumferential surfaces to which the resilient member is attached adjacent one another on the legs of the U. The resilient member 20 applies a first and second biasing force, orthogonal to the lateral nostril walls, when bent in the shape of a "U", as will be shown in greater detail subsequently.

The manufacturing process for the filter portion of the present invention consists of first producing the foam by a chemical reaction process and then removing the cell walls within the foam by a thermal or chemical process thereby producing reticulated foam. The reticulated foam consists of a three dimensional matrix with voids and intricacies within a skeletal structure.

The reticulation process removes the cell walls, leaving only a structure of skeletal strands and voids. This makes the reticulated foam exceptionally porous and permeable but with many particulate catching strands and great contaminate holding capacity within the void spaces.

The reticulated foam manufacturing process is well understood by those skilled in the field and results in a foam with consistent properties including density, tensile strength, tear strength, elongation, compression set and pore size (ppi—pores per inch).

The pores per inch specification relates directly to the efficaciousness of the filter, with a higher number relating directly to greater filtering ability and a greater breathing resistance. Current embodiments of the present invention are molded using reticulated foam of from 40 to 130 ppi so that the user may choose the best filtering characteristic based on individual need.

The reticulated foam is manufactured in large sections approximately six feet by four feet by one foot thick and then supplied to a foam fabricator skilled in the field. For current embodiments, the fabricator slits the foam to the appropriate thickness of about 0.65 inch with a 48 inch by 72 inch sheet, saws the sheet to the handling blocks of about 12 inches and then die-cuts the blocks to produce individual precurser blocks of 1 inch by 2 inches by 0.65 inch which are then further die-cut to shape approximating the semi-cylinders and connecting band suitable as a preform for the molding process. The preform is then placed in a mold and, utilizing heat and pressure, the net shape of the product incorporating the present invention is produced (including a felting step to compress the connecting band). When the product comes from the mold, the molded preform is bent to place a loft line on each of the semi-cylinders in substantially planar relation with the flexible band and the self adhesive resilient member 20 is centered, overlaid and adhered to the thin, flexible band 18 and semi-cylinders producing a product that is ready for use.

Figure 2:
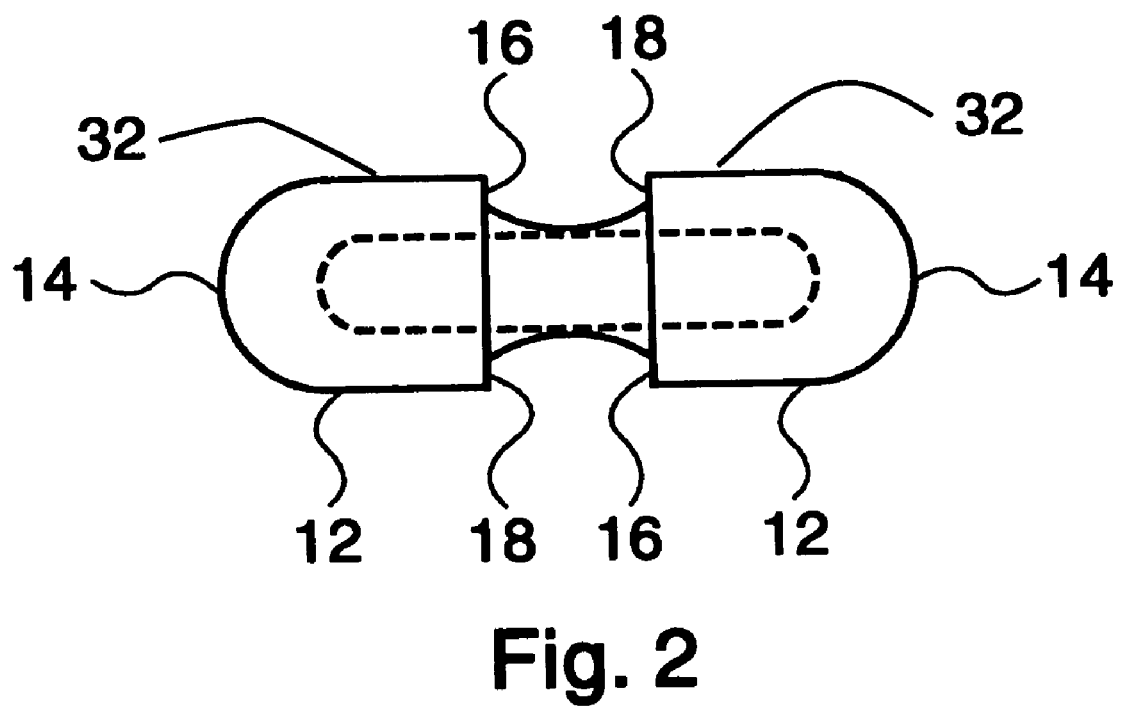
FIG. 2 is a top, plan view of the internal nasal dilator filter of FIG. 1.
Figure 3:
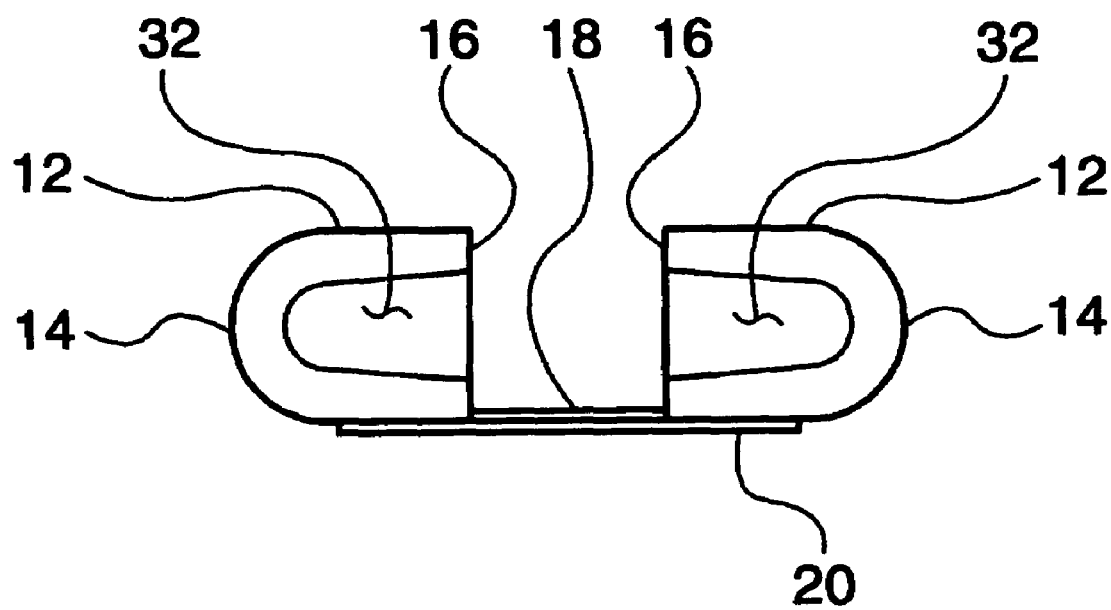
FIG. 3 is a front elevation view of the internal nasal dilator filter of FIG. 1, the rear view being a mirror image thereof.
Figure 4:
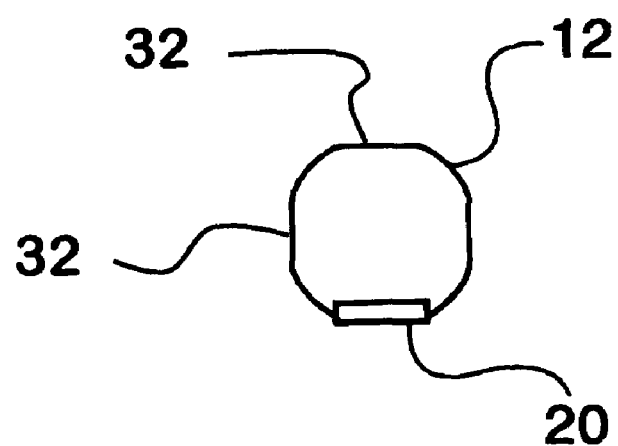
FIG. 4 is a right side elevation view of the internal nasal dilator filter of FIG. 3, the left side elevation being a mirror image thereof.

Referring to FIGS. 2 and 3, there is a slight tapering of the semi-cylindrical shape from the proximal end or base 16 to the beginning of the spherical shape 14 providing a frustoconical section. This taper and the rounding at the vertex of the distal end of the spherical shape 14 allows for an easier insertion into the nose by guiding and gently expanding and forming the nostrils during insertion. The foam employed in the embodiments of the invention is easily compressed in an axial and radial direction, whereby insertion discomfort is minimized.

Referring to FIGS. 2 and 3, the thin flexible band 18 is integrally molded to the proximal end 16 of the semi-cylindrical shapes and coincident with the centerline that joins the centers of the faces at the base 16 of the proximal ends of both semi-cylindrical shapes 12. The thin flexible band 18 has one surface in the same plane as the flat surface of the base 16 of the semi-cylindrical shapes and the other surface in a parallel plane a small distance away from the proximal end plane.

Referring to FIGS. 1, 2, 4 and 6, the thin flexible band 18 and resilient member 20 are substantially thinner and narrower than the semi-cylindrical shapes thereby allowing great conformability to the exterior of the end of the nasal septum 22. This conformity allows the base 16 of the proximal end of the semi-cylindrical shapes to be placed within the nasal vestibule just behind the narrowing of the nostril, the ala 24. The foam of the filter is so soft and gentle that when formed into the "U" shape and inserted in the nostrils, the resilient member sinks into and is cradled by the foam.

The internal nasal dilator filter is gently restrained within the nostrils so that it will not be dislodged by normal activities such as talking and eating and yet still release under the pressures of an explosive sneeze.

Again referring to FIGS. 1 and 2, the semi-cylindrical shape has a slightly flattened surface 32 on all four sides to better match the ovoid shape of the nostrils. The slightly flattened sides of the cylinders are spaced circumferentially around the frustoconical semi-cylinder and smoothly blended with the spherical shape 14 to assure a gentle yet retained fit within the nostrils.

Figure 5:
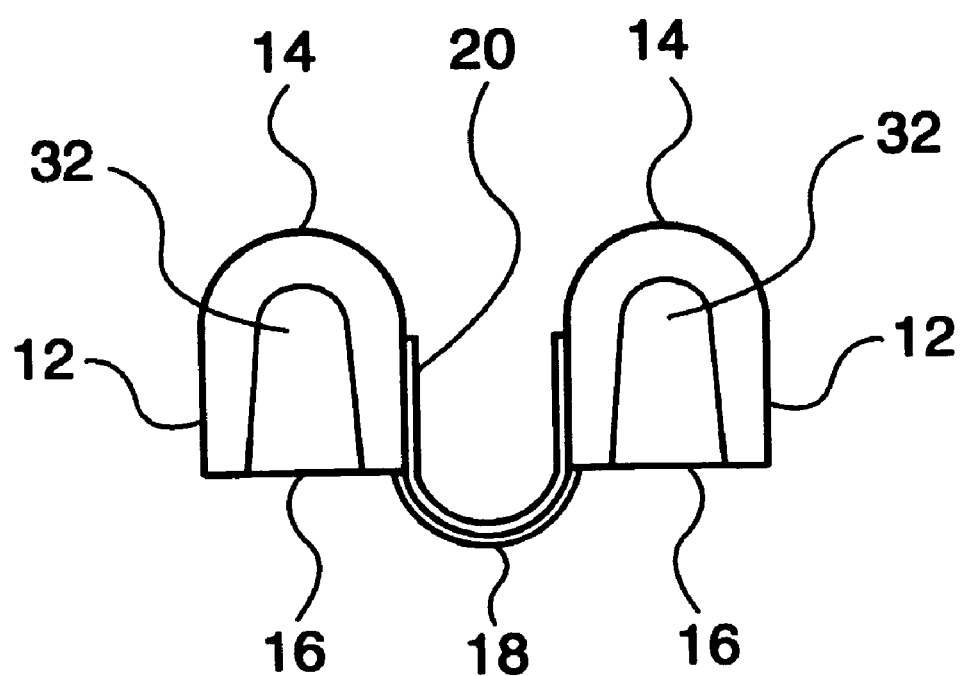
FIG. 5 is a front view of the internal nasal dilator filter of the present invention formed into a "U" shape prior to insertion in the nostrils.

FIG. 5 shows the internal nasal dilator filter 10 with the resilient member 20 formed from its normal, at rest planar shape, into a smooth "U" shape, as it would be inserted into the nostrils. The "U" shape applies first and second biasing forces at ninety degrees to the long axis of the "U". This force is applied to both the right and left of the interior nose tissue expanding and dilating the nasal air passageways. The force is cushioned by the projected width of the foam filter so there will be no irritation to the sensitive tissues of the inside of the nose.

Figure 6:
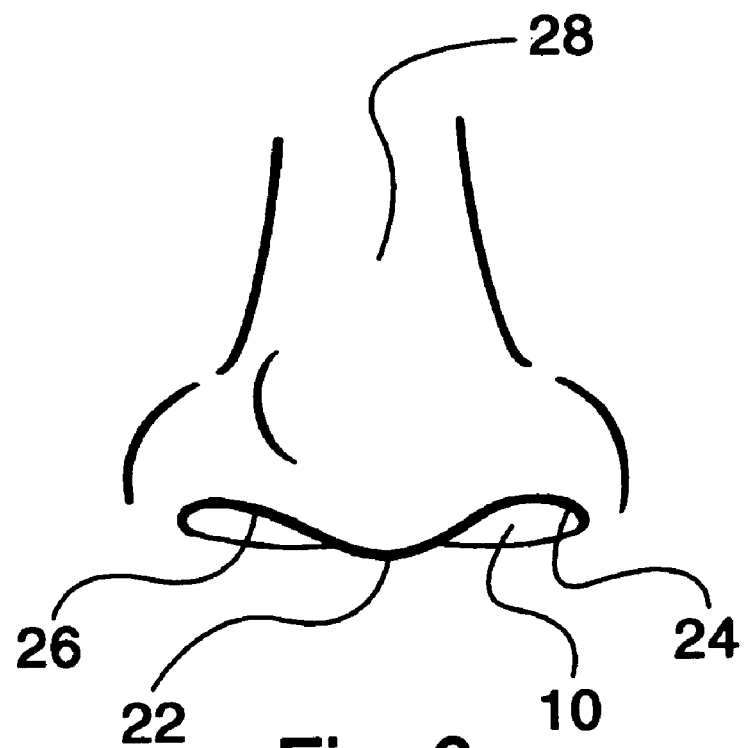
FIG. 6 is a front view of the internal nasal dilator filter of the present invention inserted in the nostrils.

Referring to FIG. 6, the internal nasal dilator filter 10 is shown inserted into the nostrils. When the device is inserted the filter foam is compressed as it passes into the vestibule area and expands to seal the nostril area. Due to the narrow shape of the resilient member with respect to the semi-cylinders, the first and second biasing forces are distributed over the rounded shape of the semi-cylinders. This then distributes the stress over a larger area and reduces the possibility of nose irritation.

Figure 7:
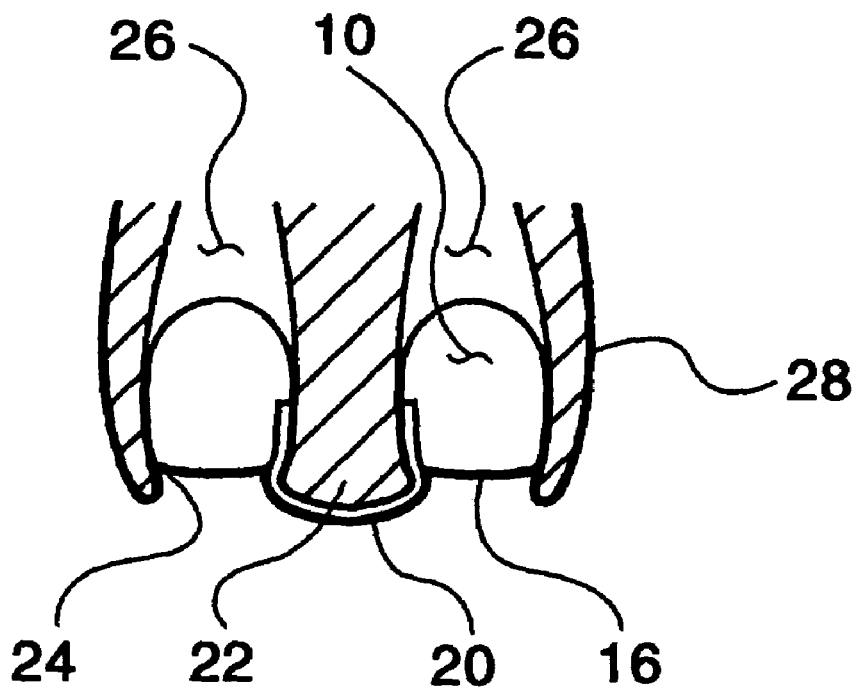
FIG. 7 is an elevation, section view of the internal nasal dilator filter of the present invention inserted in the nostrils.

Referring to FIG. 7, when installed in the nose, the internal nasal dilator filter dilates the air passages in the nostrils 24 of the nose 26 to achieve a result similar to adhesive dilators that are affixed to the exterior of the nose. The foam expansion to seal the nostrils presents a larger filter surface area and, as a consequence, lower face velocity across the filter resulting in greater filter efficiency.

Again referring to FIG. 7, the proximal ends 16 of both semi-cylindrical shapes 12 expand the nostril to conform to the shape of the filter, secure the internal nasal dilator filter to the nostril and assure that all the inhaled air passes through the reticulated air filter. The adaptability, softness and gentle expansion ability of the foam easily conforms to the resilient member and nostril to make a leak proof seal around the nostrils. The gentle expansion ability of the foam makes a nominal size suitable for many people. It is understood that the size of the may be varied in alternative embodiments to accommodate noses of other shapes and sizes.

Figure 8:
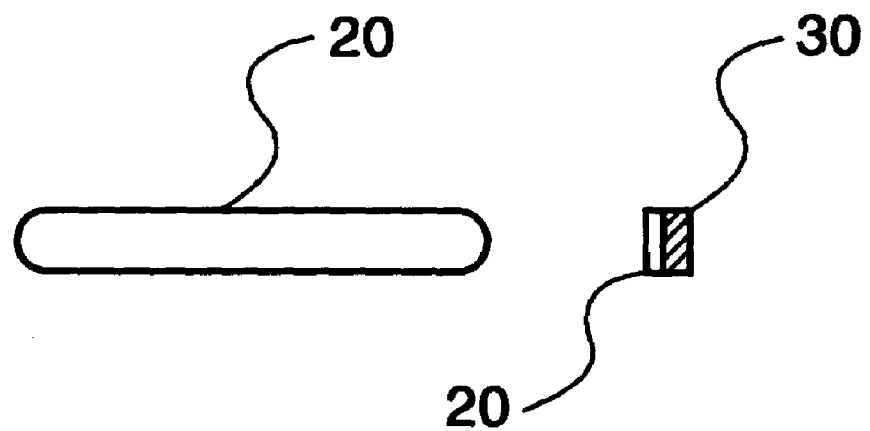
FIG. 8 is a plan and end view of the resilient member of the internal nasal dilator filter of the present invention; and, FIG. 9 illustrates a laboratory simulator used to measure the retention efficiency of the filter portion of the internal nasal dilator filter of the present invention.

Referring to FIG. 8, the resilient member 20 is indicated as a single piece for ease of visualization. In various alternative embodiments, more than one resilient member is employed and the size of the resilient member is varied in area, thickness, length, and shape. For this exemplary embodiment typical dimensions are length 1.75" by 0.010" thickness by 0.13" wide. The material of construction of the resilient member is varied in alternative embodiments but provides that the first and second biasing forces are developed orthogonally when the resilient member is bent into the "U" shape. Some materials found to be acceptable include polycarbonate (PC), polypropylene (PP), polyvinyl chloride (PVC) and acrylonyitrile butyl styrene (ABS).

The adhesive for the present embodiment is of the transfer adhesive type of high tack and strong adhesion to both the resilient member and the polyurethane filter foam.

Although several manufacturers are capable of producing an acceptable adhesive, the following 3M Medical Specialties, St Paul Minn. adhesives have been found to perform well—1509, 1512, 1522 and 1524. These adhesives are hypoallergenic, conformable and have faceside adhesive strength in the 25 to 53 oz./in. range.

Figure 9:
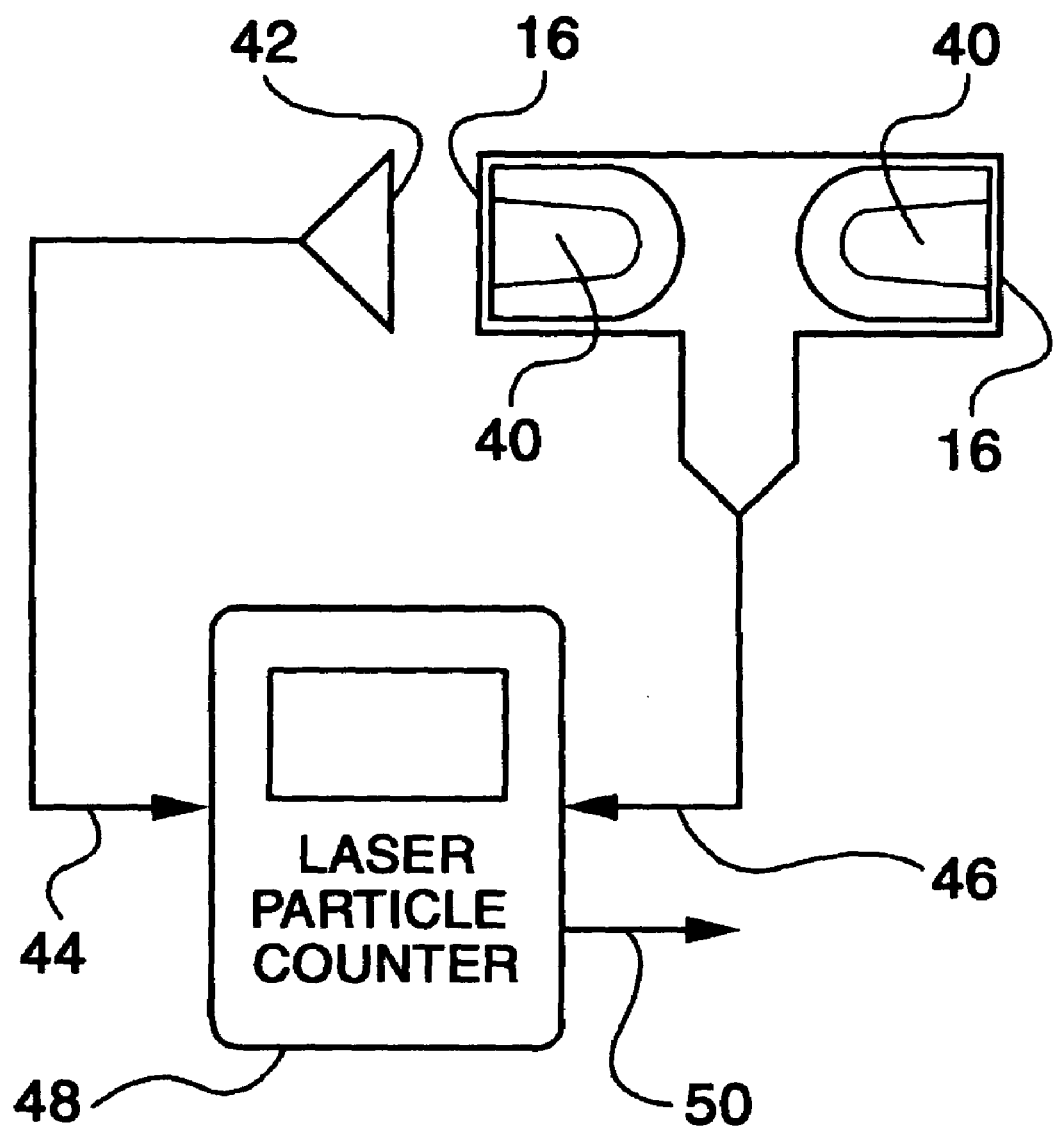

Referring to FIG. 9 the laboratory simulator is used to measure the particle retention ability or efficiency of the filter portion of the internal nasal dilator filter.

The test apparatus consists of an ambient, unfiltered air input and a filtered air input connected to a laser particle counter. The filtered air input is a tee fitting designed to accept both the right and left nostril filters of an internal nasal dilator filter whereas the ambient air input is unfiltered. Both filtered and unfiltered air inputs are connected by tubing to the laser particle counter.

The laser particle counter, model $C_{1\text{-}500}$ as manufactured by Climet Corporation, Redlands Calif., is of the manifold design so either the filtered or unfiltered input can be automatically selected during the test period. In addition, the laser particle counter measures 12 different particle size ranges at the same time while maintaining a flow rate of one cubic foot per minute (1 CFM).

A test sequence consists of automatically counting the particles in all 12 ranges in the ambient, unfiltered flow and then counting the particles in the same ranges in the filtered flow. The entire counting cycle is automatically repeated 8 times and the average particle count determined for each of the 12 ranges for both the filtered and unfiltered airflows. The retention efficiency is determined from the following formula:

Removal Efficiency (%)=(1−filtered count/unfiltered count)*100

The filter was tested in the laboratory simulator described with respect to FIG. 9 at a one cubic foot per minute (I CFM) air flow. Table 1 presents the removal efficiency percentages at each of 12 ranges for the filter portion of an internal nasal dilator filter.

It is important to specify the flow rate as a test parameter so the particle counts are taken at a normal breathing condition. If the flow rate is too low it could indicate that the pressure drop across the filter is excessive and breathing through the filter would be difficult or impossible.

Normal, at rest, breathing is approximately 12-15 times a minute at a volume of 25-30 cubic inches or 0.25 cubic feet a minute. A flow rate of 1 cubic feet per minute therefore represents a safety factor of 4 to allow for an increase in breathing rate and amount inhaled during moderate work or exercise.

TABLE 1

| Particle Size Range (microns) | Removal Efficiency (%) |
| --- | --- |
| 0.3–0.4 | 6 |
| 0.4–0.55 | 6 |
| 0.55–0.7 | 6 |
| 0.7–1.0 | 7 |
| 1.0–1.3 | 10 |
| 1.3–1.6 | 19 |
| 1.6–2.2 | 33 |
| 2.2–3.0 | 54 |
| 3.0–4.0 | 71 |
| 4.0–5.5 | 89 |
| 5.5–7.0 | 93 |
| 7.0–10.0 | 97 |

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. An internal nasal dilator filter for insertion in a user's nose comprising:
    two semi-cylinders of porous foam filter media each having a base with a flat surface and an end distal from the flat surface;
    a thin flexible band integrally molded with the semi-cylinders and extending between the bases; and
    a resilient member extending across the flexible band and onto a portion of each of the two semi-cylinders extending from the band;
    the resilient member flexibly urged into a substantially arcuate shape to place the semi-cylinders in parallel relation, the semi-cylinders sized such that upon insertion in a nostril the distal, end of each semi-cylinder is located inside the nasal vestibule and the base of each semi-cylinder is tucked in within the nostril just behind the ala, the resilient member urging the semi-cylinders against the nasal wall for outward biasing forces to each nostril so that breathing is facilitated.

2. An internal nasal dilator filter as defined in claim 1 wherein the end of each of the semi-cylinders is a spherical shape.

3. An internal nasal dilator filter as defined in claim 1 wherein the semi-cylinders are tapered from the base toward the distal end.

4. An internal nasal dilator filter as defined in claim 1 wherein the semi-cylinders have a plurality of circumferentially spaced flattened surfaces intermediate the base and distal end.

5. An internal nasal dilator filter as defined in claim 1 wherein the foam filter media is reticulated foam.

6. An internal nasal dilator filter as defined in claim 1 the resilient member is adhesively attached to the flexible band.

7. An internal nasal dilator filter as defined in claim 5 wherein the reticulated foam is selected from polyurethane or silicone chemical family and of the polyether or polyester category.

8. An internal nasal dilator filter as defined in claim 5 wherein the reticulated foam has about 40 to about 130 pores per inch.

9. An internal nasal dilator filter for insertion in a user's nose comprising:
    two semi-cylinders of foam filter media each having a base with a flat surface and a spherical shape on an end distal from the flat surface, the semi-cylinders tapered from the base toward the distal end, and have a plurality of circumferentially spaced flattened surfaces intermediate the base and distal end; and,
    a thin flexible band integrally molded with the semi-cylinders and extending between the bases;
    a resilient member extending across the flexible band and onto a portion of each of the two semi-cylinders extending from the band;
    the resilient member flexibly urged into a substantially arcuate shape to place the semi-cylinders in parallel relation, the semi-cylinders sized such that upon insertion in a nostril the distal, spherical shaped end of each semi-cylinder is located just inside and within the nasal vestibule and the base of each semi-cylinder is tucked in within the nostril just behind the ala, the resilient member urging the semi-cylinders against the nasal wall for outward biasing forces to each nostril so that breathing is facilitated.

10. An internal nasal dilator filter as defined in claim 9 wherein the foam filter media is reticulated foam.

11. An internal nasal dilator filter as defined in claim 9 wherein the resilient member is adhesively attached to the flexible band.

12. An internal nasal dilator filter for insertion in a user's nose comprising:
    two foam filters each extending from a base with a flat surface;

a thin flexible band extending between the bases; and a resilient member extending across the flexible band and onto a portion of each of the two foam filters extending from the band;

the resilient member flexibly urged into a substantially arcuate shape to place the foam filters in parallel relation for insertion into the nostrils, the resilient member urging the foam filters against the nasal wall for outward biasing forces to each nostril so that breathing is facilitated.

13. A method for producing an internal nasal dilator filter comprising the steps of:

selecting reticulated foam in sheet form;

slitting the foam to a predetermined thickness;

sawing the foam to a predetermined dimension;

die-cutting the foam to produce a preform suitable for a molding process;

molding the preform utilizing heat and pressure to a net shape having two semi-cylinders of reticulated foam filter media each having a base with a flat surface and a spherical shape on an end distal from the flat surface and a thin flexible band integrally molded with the semi-cylinders and extending between the bases attaching a resilient member to the flexible band and a portion of each of the semi-cylinders.

14. A method for producing a internal nasal dilator filter as defined in claim 13 wherein the step of selecting reticulated foam comprises selecting foam from the polyurethane or silicone chemical family and of the polyether or polyester category.

15. A method for producing an internal nasal dilator filter as defined in claim 13 wherein the step of selecting reticulated foam further comprises selecting foam having about 40 to about 130 pores per inch.

16. A method for producing an internal nasal dilator filter as defined in claim 13 wherein the step of attaching the resilient member comprises the steps of:

bending the molded preform to place a loft line on each of the semi-cylinders in substantially planar relation with the flexible band;

adhesively bonding the resilient member to the flexible band, the ends of the resilient member extending along the loft lines of the semi-cylinder for a portion of their length.

* * * * *